(12) United States Patent
Ridgeway et al.

(10) Patent No.: US 6,178,810 B1
(45) Date of Patent: *Jan. 30, 2001

(54) CRUDE OIL MEASUREMENT SYSTEM AND METHOD

(75) Inventors: Richard L. Ridgeway, Odem, TX (US); John W. Sulton, Tulsa; Scott D. Graham, Bristow, both of OK (US)

(73) Assignee: Micro Motion, Inc., Boulder, CO (US)

( * ) Notice: Under 35 U.S.C. 154(b), the term of this patent shall be extended for 0 days.

This patent is subject to a terminal disclaimer.

(21) Appl. No.: 09/112,565

(22) Filed: Jul. 9, 1998

Related U.S. Application Data

(63) Continuation of application No. 08/805,214, filed on Feb. 27, 1997.

(51) Int. Cl.⁷ .......................... G01N 33/26; F02M 33/02; G06F 7/04
(52) U.S. Cl. .................................. 73/53.05; 340/825.36; 123/516
(58) Field of Search ............................. 73/53.05, 119 A; 340/825.36; 123/516

(56) References Cited

U.S. PATENT DOCUMENTS

| | | |
|---|---|---|
| 2,613,535 | 10/1952 | Born . |
| 3,373,609 | 3/1968 | Sundby . |
| 3,867,056 | 2/1975 | Carle et al. . |
| 4,101,056 | 7/1978 | Mattimoe et al. . |
| 4,404,847 * | 9/1983 | Larson ............................... 73/119 A |
| 4,551,719 * | 11/1985 | Carlin et al. ..................... 340/825.36 |
| 4,651,788 | 3/1987 | Grosskreuz et al. . |
| 4,716,771 | 1/1988 | Kane . |
| 4,720,998 | 1/1988 | Hogue . |
| 4,773,257 | 9/1988 | Aslesen et al. . |
| 4,782,711 | 11/1988 | Pratt . |
| 4,915,145 | 4/1990 | Schirmacher . |
| 4,981,175 | 1/1991 | Powers . |
| 5,115,683 | 5/1992 | Pratt . |
| 5,297,423 | 3/1994 | Keating et al. . |
| 5,349,994 | 9/1994 | Koeninger . |
| 5,351,725 | 10/1994 | Suthergreen et al. . |
| 5,355,860 * | 10/1994 | Ekstram ............................... 123/516 |
| 5,404,923 | 4/1995 | Yamamoto et al. . |
| 5,471,867 | 12/1995 | Tuma et al. . |
| 5,487,300 | 1/1996 | Brackett et al. . |
| 5,615,702 * | 4/1997 | Dawans et al. ...................... 137/255 |
| 5,757,664 * | 5/1998 | Rogers et al. ....................... 364/509 |

FOREIGN PATENT DOCUMENTS 2 706 578 * 12/1994 (FR) ............................... F17C/5/00

OTHER PUBLICATIONS

FLOW–TEK, INC. brochure on 3–Way Multiport Ball Valves;.
Smith Meter Inc. brochure on Mass Flow and Density Sensors;.
Smith Meter Inc. brochure on Micro–Pak Transmitter Module;.
GM&C/Read Truckloading brochure.

\* cited by examiner

Primary Examiner—Hezron Williams
Assistant Examiner—Jay L. Politzer
(74) Attorney, Agent, or Firm—Shook, Hardy & Bacon L.L.P.

(57) ABSTRACT

A system for measuring crude oil as it is transported from a storage tank to a transport vessel. The transport vehicle includes a fluid conveying line adapted to extend from the storage tank to the transport vessel. A pump is connected to the line to convey the oil from the tank to the vessel. A mass meter is disposed in the line. A microprocessor is electrically connected to and controls the mass meter so as to calculate the volume of liquid transferred from the storage tank to the transport vessel. A sample pot device is connected to the line and capable of taking an oil sample from the line that is representative of the entire amount of oil that is transferred.

10 Claims, 4 Drawing Sheets

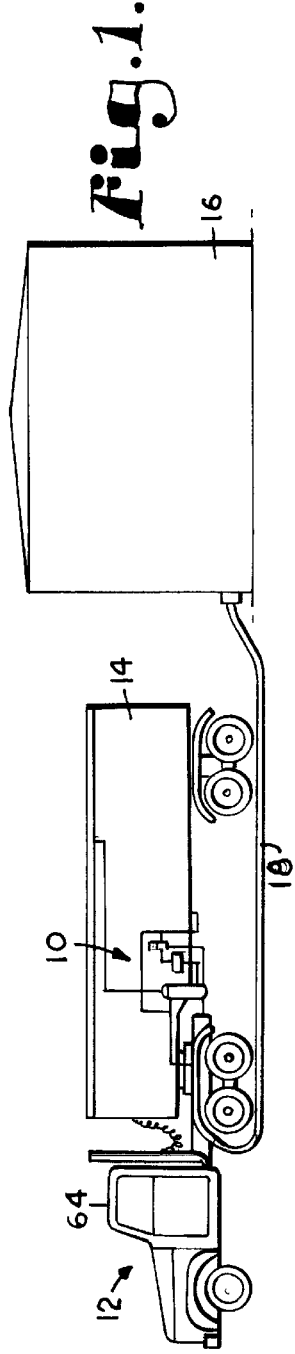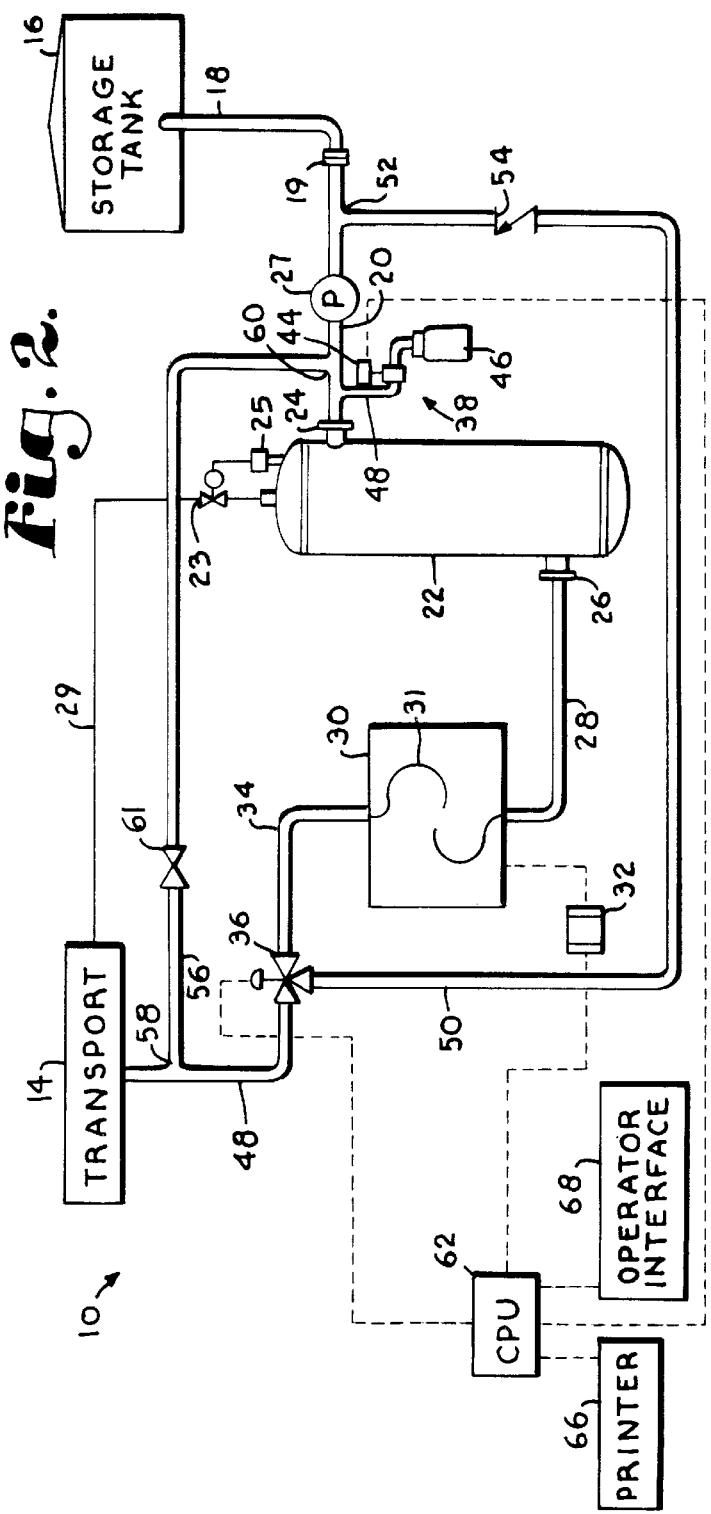

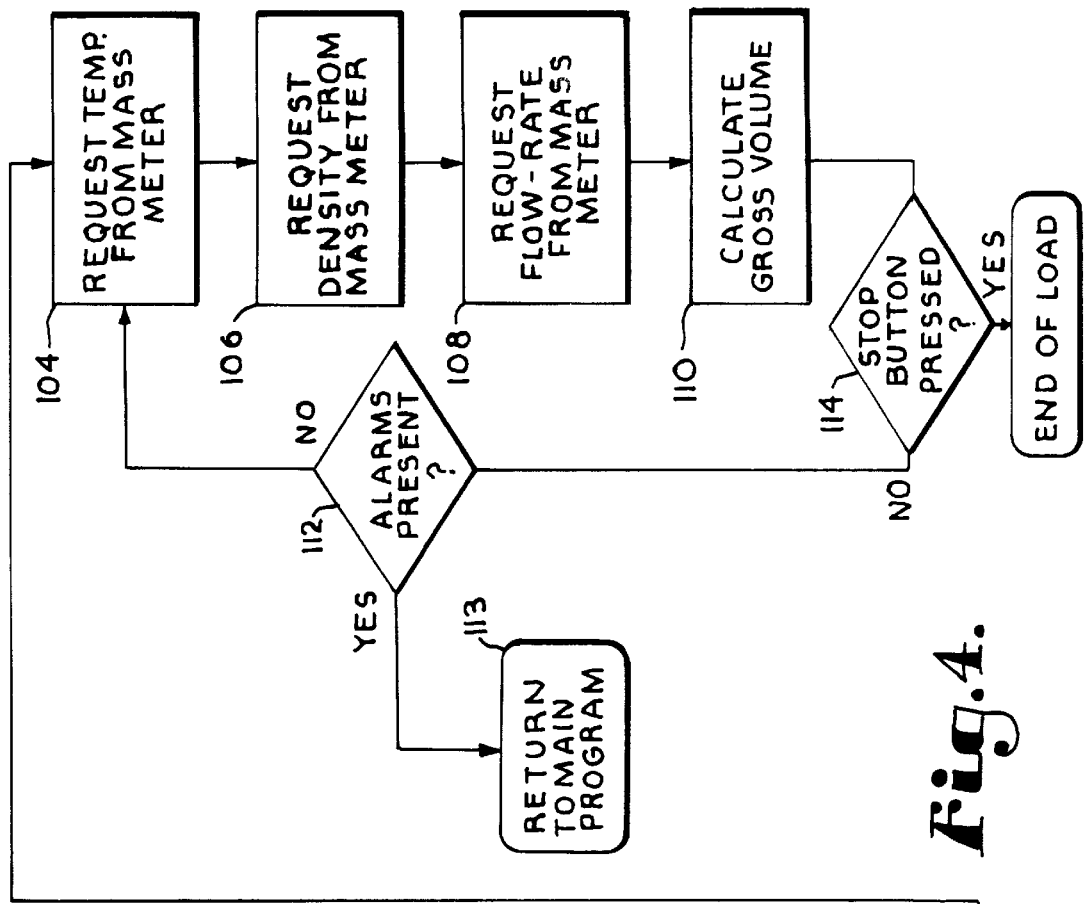
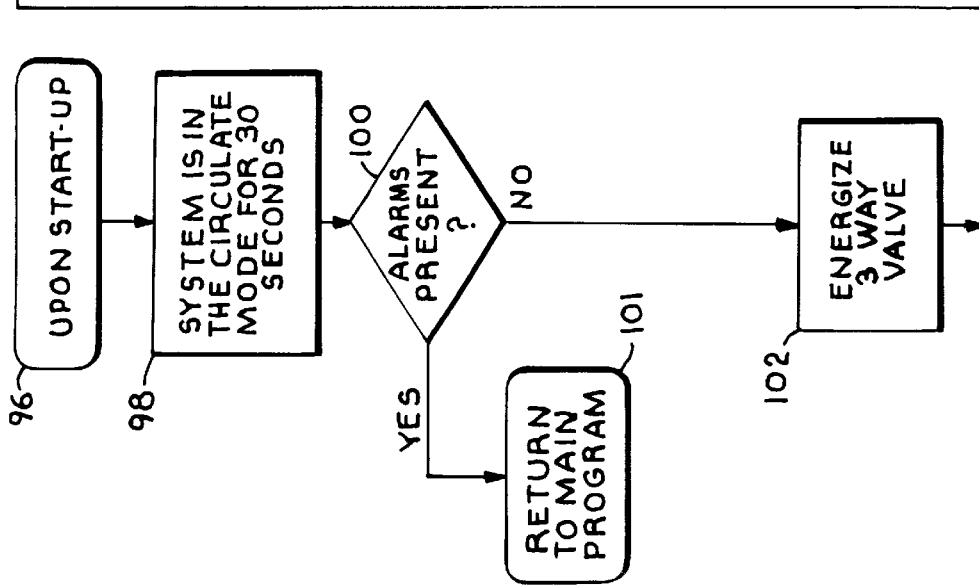
Fig. 4.

CRUDE OIL MEASUREMENT SYSTEM AND METHOD

CROSS REFERENCE TO RELATED APPLICATIONS

This application is a continuation of application Ser. No. 08/805,214, filed with the U.S. Patent and Trademark Office on Feb. 27, 1997.

STATEMENT REGARDING FEDERALLY-SPONSORED RESEARCH OR DEVELOPMENT

Not applicable.

BACKGROUND OF THE INVENTION

This invention relates to a system and a method for measuring crude oil, and, more particularly, to a system for accurately measuring oil as it is transferred from a lease storage tank to a transport vehicle.

Currently, oil extracted from the ground is stored on the lease site in one or more storage tanks, often collectively called tank batteries. These storage tanks typically are large cylindrical vessels into which the oil is pumped via a pump jack or other extraction structure. Periodically, the oil must be transferred from the storage tanks to a refinery or central storage area. Usually, the oil produced on a particular lease is the property of a particular producer and landowner. The oil is typically purchased from these entities by a refining company. The refining company collects the oil from the leaseholds via transport tanker trucks. As is apparent, it is necessary for the refining company to keep track of the amount of oil obtained from a particular leasehold so that the lease producer and landowner can be adequately compensated.

Currently, oil is collected in the same manner it has been for the last fifty years. A transport truck is pulled close to a storage tank and coupled thereto via a valve system. Prior to loading, however, certain parameters are needed from the storage tank. More specifically, tables are available for the cross-sectional size of the tank such that the volume of oil in the tank can be computed by measuring the height of the oil prior to loading and the height of the oil after loading is completed. However, other factors can also affect the volume of the oil transferred from the tank, such as its density and temperature.

In a typical loading process, a tanker truck operator prior to transferring oil from the storage tank to the tanker truck will take temperature, gravity (density), height, encrustation readings and basic sediment and water content. More specifically, prior to the loading onto the transport vehicle, an operator must climb to the top of the tank to take various readings from the oil inside. Tanks usually have hinged vent lids on the top which allow the operator access to the interior of the tank from the upper surface of the tank. A ladder and/or catwalk structure is utilized to allow the operator access to these vents. Therefore, an operator must climb to the top of the tank to take these readings. A temperature reading is taken by lowering a wood back thermometer to the center of the tank for approximately fifteen minutes and then retracting the thermometer and noting the temperature reading. Thus, the temperature only is taken at one particular level in the tank. Unfortunately, there can be various temperature gradients within the tank, for instance, depending upon whether the temperature is taken on the sunny or shady side of the tank. This is exacerbated by the fact that the access vents discussed above are typically adjacent one edge of the tank.

Further, while a temperature reading is being taken, a sampling device known as a "thief" typically will be lowered into the tank to a level adjacent the bottom of the tank to take an oil sample which is then retrieved from the tank indicating the bottom in the tank. The thief also will be lowered into the tank at predetermined levels to detect the basic sediment and water content of the oil and to define the observed gravity. Thereafter, the operator will lower a hand-operated gauge line into the tank to determine the height of the column of oil in the tank. The operator will then climb down from the tank and proceed to the cab of the transport truck with the gathered information. The oil sample is analyzed by the operator to determine the density of the oil in the tank. Further, the oil sample is centrifuged to get a representative reading of the sediments and water in the tank. Additionally, when the operator is on the tank, the level of encrustation on the tank wall adjacent the vent lid is noted. More specifically, the amount of buildup (such as rust) on the wall of the tank is noted. Thereafter, the operator leaves the cab of the truck and begins to unload the oil from the storage tank to the tanker truck.

After the tanker truck reaches a full level, loading is stopped. The operator then returns to the top of the tank and takes another oil level reading utilizing the gauge line. The operator also takes the observed temperature and checks bottom levels. The operator then returns to the truck with this last piece of information, and, thereafter, computes the net volume of oil transferred utilizing the temperature reading, density reading, oil level difference, sediment and water readings, and encrustation value. As is apparent, there are numerous inaccuracies associated with this collection method. First of all, the temperature is taken at only one level when there can be numerous temperature gradients throughout the oil contained in the storage tank. Further, the sample utilized to determine gravity and the sediment and water values is also only taken at predetermined levels depending on tank size. These values can also vary greatly throughout the volume of oil contained in the storage tank. Still further, the encrustation value taken at the vent lid is utilized in conjunction with a table to determine the approximate amount the volume should be reduced due to encrustation throughout the entire tank. As is apparent, this one value from one particular point in the tank does not provide a very accurate reading as to the amount the volume should be decreased due to encrustation. A further error in the readings results from the adhesion of the oil to the inside surface of the storage tank. More specifically, as oil is removed from the storage tank, a certain amount of oil will adhere to the tank's inner surface as the oil is removed from the bottom of the tank. This oil adhered to the sides will take a substantial amount of time to return to the main body of oil. Therefore, because the second depth reading is taken immediately after loading, a substantial amount of the oil adhered to the side has not returned to the main body of oil. Thus, this oil is computed as being removed from the tank when in fact it has not been removed.

A further disadvantage of the current transfer method involves the collection of oil having a high sulfur content. More specifically, with oil having an $H_2S$ content of 300 parts per million (ppm) and higher, current safety standards require that at least two tank truck operators be present during collection. More specifically, because an operator has to climb up onto the tanks and physically have access to the interior of the tanks, the possibility exists of the operator being overcome by fumes from the tank. Therefore, while one operator is on the tank, another must remain at ground level. Further, because of the high sulfur value, the operator accessing the tank interior must don appropriate safety equipment, such as masks and gloves, each time access to the tank is desired. Therefore, the operator must don the safety equipment prior to initially climbing up onto the tank, and must further don the equipment later when the final height value is taken from the tank. Therefore, the donning and removal of the safety equipment adds additional time to an already cumbersome and time-consuming transfer process.

As is apparent, the current transfer system has numerous inaccuracies associated therewith which can result in mistrust between the refining company and the producer/landowner. Further, the steps of the current transfer procedure are very cumbersome and require a substantial amount of time and effort on the part of the persons collecting the oil. Therefore, a novel crude oil transfer system is needed which alleviates the above-discussed drawbacks of the current transfer procedures.

BRIEF SUMMARY OF THE INVENTION

Accordingly, it is an object of the present invention to provide a crude oil measuring system and method which accurately determines the amount of oil transferred from a lease storage tank to a transport vehicle.

Another object of this invention is to provide a crude oil measurement system and method which decreases the amount of time required during transfer of crude oil from the storage tank to the transport vehicle.

Yet another object of the present invention is to provide a crude oil measurement system which accurately takes an oil sample to determine the sediment and water values of the oil being transferred.

A further object of this invention is to provide a crude oil measurement system and method which eliminates the need to utilize two transport vehicle operators to collect oil.

Yet another object of the present invention is to provide a crude oil measurement system and method which allows more accurate and representative measurement of the temperature, density, sediment, and water parameters of oil contained in a storage tank.

Another object of the present invention is to provide a crude oil measurement system and method which eliminates air from a closed transfer system prior to crude oil being transferred from the storage tank to the transport vehicle.

A further object of the present invention is to provide a crude oil measurement system which allows automatic stoppage of oil transfer when water is automatically detected by the transfer system.

Accordingly, the present invention provides for a system for measuring crude oil as it is transferred from a storage tank to a transport vessel of a transport vehicle. The system includes an oil conveying line adapted to extend from the storage tank to the transport vessel. A pump provided on the transport vehicle is connected to the line to convey oil from the tank to the transport vessel. A mass meter is also connected to the conveying line. A microprocessor is electrically connected to and controls the mass meter so as to calculate the volume of liquid transferred from the storage tank to the transport vessel. A sample pot is also connected to the conveying line. The sample pot is electrically coupled to the microprocessor and is capable of taking an oil sample from the conveying line proportionate to the flow rate that is representative of the entire amount of oil that is transferred.

BRIEF DESCRIPTION OF THE DRAWINGS

In the accompanying drawings which form a part of this specification and are to be read in conjunction therewith and in which like reference numerals are used to indicate like parts in the various views:

FIG. 1 is a diagrammatic representation of the connection between a crude oil storage tank and a crude oil transport truck;

FIG. 2 is a diagrammatic view showing the crude oil measurement system of the present invention;

FIG. 4 is a flow chart depicting the load sequence performed by the microprocessor.

DETAILED DESCRIPTION OF THE PREFERRED EMBODIMENTS

Figure 3:
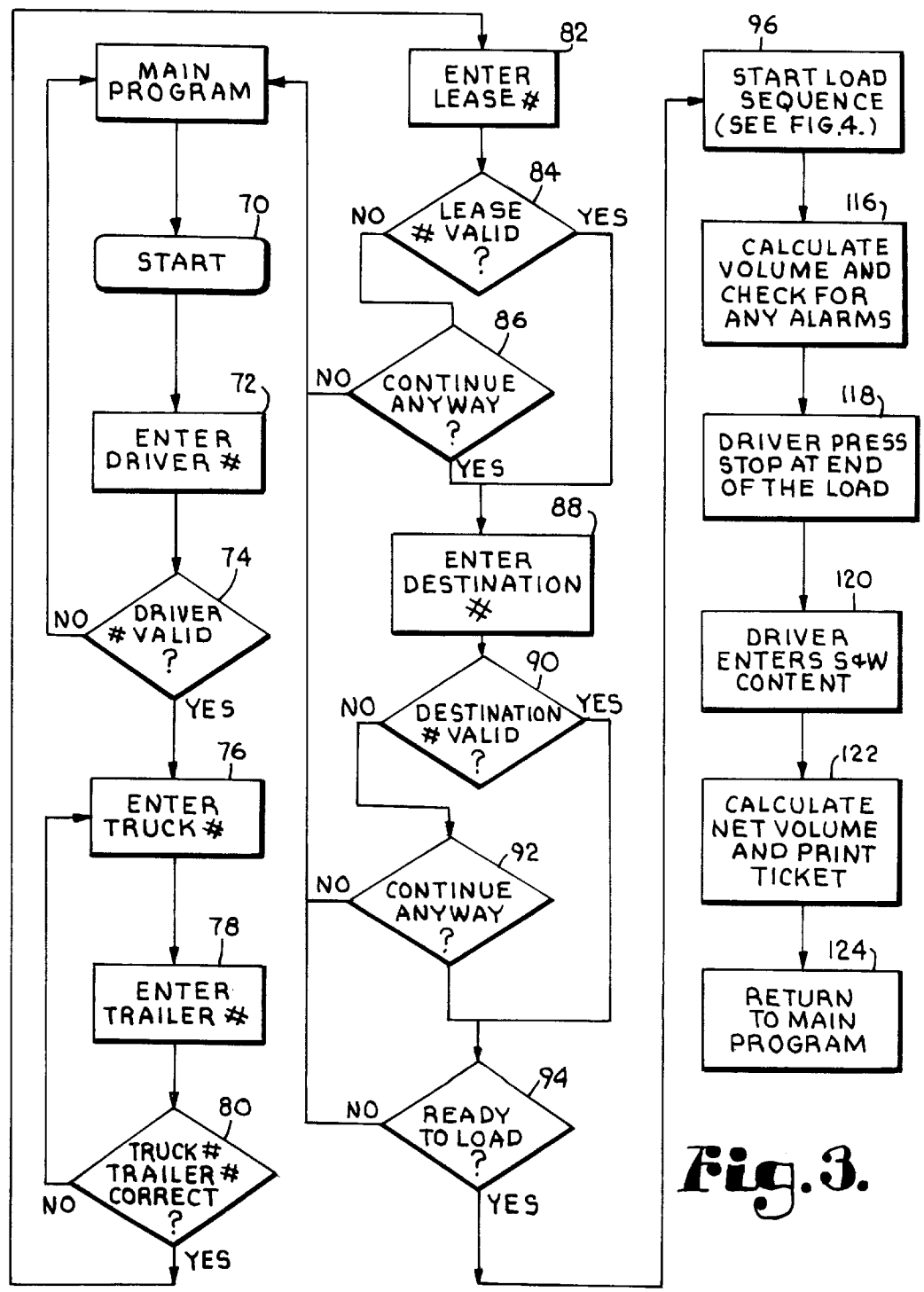
FIG. 3 is a flow chart depicting the steps utilized to effectuate transfer of the crude oil from the storage tank to the transport vehicle, and, in particular, the steps performed by the microprocessor controlling the overall measurement system.

Referring to the drawings in greater detail, and initially to FIGS. 1 and 2, a crude oil measurement system 10 is shown. System 10 is completely contained on a transport vehicle 12. Vehicle 12 has a transport vessel 14 that is utilized to contain oil after it has been transferred from lease storage tanks 16. Generally, oil is transferred from tank 16 to vessel 14 via a conveying hose 18. Prior to the oil entering vessel 14, it is conveyed through system 10 to determine the net volume of oil conveyed from tank 16 to vessel 14. A conveying line or pipe section 20 is connected to hose 18 with a coupling 19 and is also connected to an air elimination vessel or structure 22. A reversible pump 27 is disposed in line section 20 and is utilized to convey oil from tank 16 to transport vessel 14. Air eliminator structure 22 has an input port 24 connected to line section 20. Air elimination structure 22 also has an output port 26 to which a conveying line section 28 is connected. The purpose of structure 22 is to remove air from system 10 especially during the startup of the system and prior to the transporting of any oil to vessel 14. Structure 22 is generally a vertically disposed cylindrical tank with a vent line 29 extending from its upper surface and running to the interior of vessel 14. One type of air eliminating vessel 22 suitable for the present system can be obtained from Trailmaster, Inc., of Ft. Worth, Tex., and preferably has a design pressure of 60 PSIG at 180° F.

Figure 5:
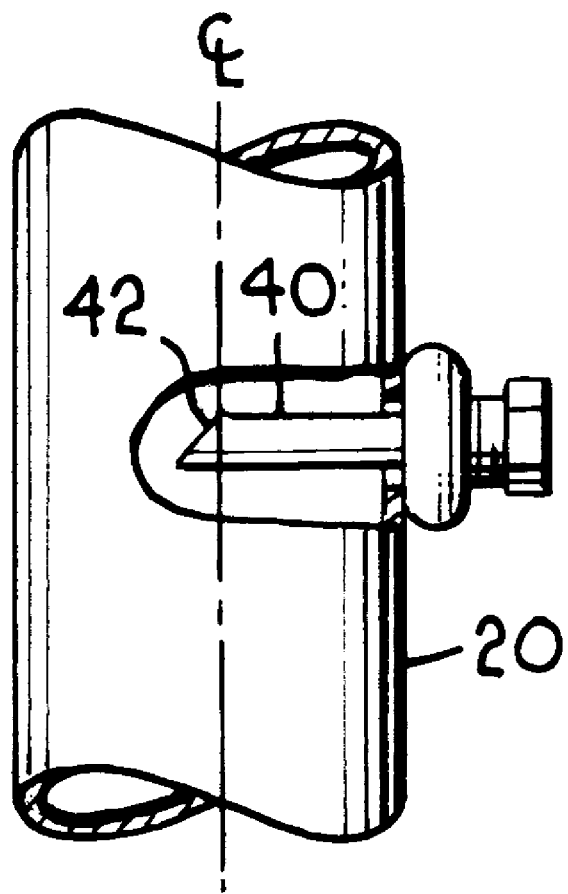
FIG. 5 is a detailed cross section of a sample probe of the sample pot device.

Disposed in line section 20 is a sampling pot device 38. Sampling device 38 allows the taking of periodic oil samples during transfer of oil from tank 16 to vessel 14. From this sample, standard or average water and sediment values can be obtained. With reference to FIG. 5, sampling device 38 includes a mounted sampling probe 40 in line section 20. An open end 42 of probe 40 is generally positioned in the geographic center of line section 20. Additionally, open end 42 generally faces but is angled toward the oncoming flow of oil through line section 20. Probe 40 is connected to a sampling solenoid 44 which will be actuated periodically to take a small sample of oil flowing through line section 20 in a manner that will be further described below. Also attached to sample solenoid 44 is a sample container 46. It has been found that a 12-volt electric solenoid manufactured by Peter Paul Electronics Co. of New Britain, Conn., under the Model No. E26HH92CCM, with a volume regulator manufactured by Chemco of Tulsa, Okla., offers a suitable solenoid sampling combination. The volume regulator serves to measure the periodic sample and convey it to container 46. Further, it has been found that container 46 can be of a 2-quart regulated pressure-type container manufactured by Cliff Mock Co. of Houston, Tex., under the Model No. R2P.

After line section 28 leaves structure 22, it is connected to a mass meter 30. Mass meter 30 is of a Coriolis type and is used to measure the density, temperature, and mass flow rate of oil flowing therethrough. Coriolis meters are very nonintrusive to the flow of liquid therethrough and operate by measuring the effects of Coriolis forces on a pair of S-tubes (shown generally at 31), which are electromagnetically vibrated. The measurement principle is based on a variation of Newton's Second Law of Motion:

$$Force = Mass \times Acceleration.$$

As fluid proceeds through the S-tubes, it experiences an acceleration transverse to the direction of flow, and Coriolis forces result. The Coriolis force causes the displacement of the vibrating tubes to become slightly distorted or out of phase. Motion sensors are placed symmetrically about the midpoints of the vibrating tubes and generate electrical signals with a relative phase shift that is proportional to mass flow. These electrical signals are processed by a transmitter module 32 which is electrically connected to mass meter 30. The frequency of vibration also varies with fluid density and temperature sensors can also be present. Therefore, transmitter module 32 can also measure this frequency and thereby provide a density and temperature output. A type of mass meter that has been found suitable for this application is a mass meter manufactured under the trademark S-MASS, manufactured by Smith Meter, Inc., of Erie, Pa. Further, a suitable transmitter module 32 is manufactured under the trademark MICRO-PAK, also available from Smith Meter, Inc., of Erie, Pa.

Exiting mass meter 30 is conveying line section 34. Line section 34 connects mass meter 30 to a diverting value 36. Diverting valve 36 is preferably of a three-way multiport ball valve variety. Valve 36 is preferably automatically operated by a solenoid. One such valve that has been found to operate suitably is a valve manufactured under the Model No. MPF15 by Flow-Tek, Inc. of Columbia, S.C.

In addition to conveying line 34, valve 36 is also connected to conveying line section 48 and recirculation conduit 50. Conveying line section 48 is connected to the interior of transport vessel 14 and serves as a final conveyance structure of oil from tank 16 to transport 14. Recirculation conduit 50 runs from valve 36 back to a T-connection 52 in conveying line section 20. Connection 52 is generally on the suction side of pump 27 when pump 27 is in the mode to transfer oil from tank 16 to vessel 14. Disposed in conduit 50 is a check valve 54 which only allows flow in the direction from diverting valve 36 to connection 52.

Valve 36 has two different positions. A first position allows flow from line section 34 to line section 48 while blocking flow to conduit 50. When valve 36 is in this first position, oil will be introduced into transport vessel 14. A second position of valve 36 allows flow from line section 34 to recirculation conduit 50 while blocking flow to line section 48. When valve 36 is in the second position, system 10 is in its recirculation mode as will be more thoroughly described below.

Conveying line section 48 also has an unloading line or pipe 56 attached thereto at a T-connection 58. The other end of unloading line 56 is connected to conveying line section 20 at a T-connection 60. Unloading line 56 has a manually actuated valve 61 disposed therein. Line 56 is used to unload oil that has been transported in vessel 14 to a central storage facility or refining facility. More specifically, valve 61 during the conveying from storage tank 16 to vessel 14 is closed such that no oil flows through line 56. However, when the storage facility or refining facility is reached by the transport vehicle, it is necessary to unload the oil therefrom. However, it is not necessary to thereafter meter the oil being unloaded. Therefore, to unload oil from vessel 14, the central storage tank or refinery tank is connected via a hose at coupling 19. Valve 61 is actuated manually to its open position, and valve 36 is positioned in its second position such that no backflow can occur past valve 36 in conveying line section 48. Additionally, pump 27 can thereafter be reversed to unload oil through line 56, line section 20 and out coupling 19.

Pump 27, air eliminator structure 22, mass meter 30, diverting valve 36, and sampling device 38 are all preferably located on the chassis of transport vehicle 12 such that system 10 is conveyed with the transport vehicle from leasehold to leasehold.

Pump 27, mass meter 30, diverting valve 36 and sampling device 38 are all electrically connected to and controlled by a central processing unit (CPU) or microprocessor 62. CPU 62 is preferably located in the cab 64 of transport vehicle 12 and has a connected printer 66 and an operator interface 68 such as a keyboard and display. Interface 68 allows the system operator to input various lease and destination information into the CPU and also to monitor various information as the system is operating. CPU 62 has a program which prompts the system operator to enter various important information and thereafter operates and controls the entire system during the transfer of oil from storage tank 16 to transport 14. CPU 62 further collects and calculates the needed information so that a ticket conveying the volume of oil transferred can be printed at printer 66.

With reference to FIGS. 3 and 4, the operation of the entire system 10 and its interface with CPU 62 will be described. First, an operator pulls transport vehicle 12 adjacent a storage tank 16 and connects tank 16 to system 10 via hose 18. Thereafter, through operator interface 68, the main operating program of CPU 62 is started as indicated at 70 in FIG. 3. The operator is prompted by the CPU to enter his or her driver number into the computer as indicated at 72. The CPU determines whether this is a valid driver number from a list of preprogrammed driver numbers as indicated at 74. If it is not a valid driver number, the program returns to the initiation of the main program. If it is a valid number, the operator is then asked to enter the truck and trailer number as indicated at 76 and 78. If the numbers are not correct, the operator is again prompted to enter the proper truck and trailer number as generally shown at 80. If the truck and trailer's numbers are correct, the operator is then prompted to enter the lease number as shown at 82. The CPU then determines whether the lease number is valid from a list of predetermined lease numbers stored in the CPU. If the lease number is not valid, the operator is given the option of continuing anyway as shown at 86.

In the next step, the operator is prompted to enter the destination of the oil that is to be loaded, as generally shown at 88. Again, the CPU determines whether the destination number is valid from a list of predetermined destination numbers as shown at 90. If the destination number is not valid, the operator is again given the option of continuing anyway as shown at 92. Thereafter, the operator is prompted to indicate whether or not he or she is ready to begin loading, as generally shown at 94.

Thereafter, the load sequence shown in FIG. 4 is actuated in the CPU, as generally shown at 96. As a first step 98, the system is put into a recirculation mode to eliminate air therefrom so that the accuracy of the system is increased. The recirculation mode lasts for at least 30 seconds. In this recirculation mode, diverting valve 36 is in its second position such that flow is allowed from line section 34 to recirculation conduit 50. Further, pump 27 is actuated. Therefore, oil is taken from storage tank 16 via hose 18 and conveyed through conveying line section 20, through air elimination structure 22, through conveying line section 28, through mass meter 30, through conveying line section 34, through diverting valve 36, through recirculation conduit 50, through check valve 54, and back to line section 20 at T-connection 52. Connection 52 is at the suction side of pump 27 when pump 27 is operating in the mode to transfer from tank 16 to transport vessel 14. Therefore, oil is circulated through the above circuit continuously without any of it being propelled to transport vessel 14. The purpose of this recirculation is to eliminate air in the system and, thus, get more accurate readings out of mass meter 30. Air eliminator 22 is the structure that accomplishes this. More specifically, oil is conveyed into structure 22 at the input port 24 that is vertically located above the output port 26. As oil flows through structure 22 from port 24 to port 26, air that is within the oil will naturally go to the highest point within the structure. At the top of this structure is vent line 29. Vent line 29 has a solenoid actuated check valve 23 disposed therein. Valve 23 allows air or vapor to pass therethrough in one direction only such that the air or vapor is conveyed to transport vessel 14. A level detector 25 is also positioned at the top of structure 22. Air or vapor in structure 22 will continue to flow upwardly through vent line 29 until such point that the oil reaches the top of the eliminator and is detected by detector 25. Detector 25 then signals valve 23 to close so that no vapor or liquid is thereafter allowed upwardly through vent 30. Mass meter 30 then checks to determine whether there are any additional air bubbles left in the system. More specifically, the mass meter automatically senses whether air is present therein, and if so, goes into an "overdrive" state where measurement cannot be taken. The CPU senses this overdrive state. Further, a value for the density of water is inputted into the CPU such that the values read from mass meter 30 can be compared with the water density value. The CPU then makes a determination whether there is water or air present in the system. If there is water or air present, the CPU will actuate an alarm as indicated generally at 100 in FIG. 4. More specifically, a visual indicator will be relayed to the operator on interface 68 and the CPU will return to the beginning of the main program as indicated at 101. At that point, the operator can be given the option to continue (not shown) and override the alarms. This operator determination is made on the basis of inspection of the oil in the storage tank to determine if the amount of water therein makes it undesirable to collect the oil therefrom.

If no alarms are present at 100, the CPU energizes diverting valve 36 to its first position, as generally shown at 102. More specifically, valve 36 is energized such that flow is allowed from line section 34 to line section 48 and flow is blocked to conduit 50. At the time of the energizing of valve 36, the measuring at mass meter 30 also begins to take place, and, further, the sampling at sampling device 38 also begins. More specifically, when valve 36 is in its first position, oil flows from tank 16 through hose 18, through line section 20 (which contains sampling device 38), through eliminator 22, through line section 28, through mass meter 30, through line section 34, and through line section 48 into transport vessel 14. This generally is the transfer path of oil from storage tank 16 to transport vessel 14. During transfer, the CPU will continuously gather and request temperature, density and flow rate values from mass meter 30 through transmitter 32 as generally depicted at reference numerals 104, 106, and 108, respectively. From the values gathered by the CPU, a running total of the gross volume will be calculated as shown at 110. In addition to calculating the gross volume that flows through the mass meter, the CPU is also checking to see whether any detrimental conditions exist, as generally shown at 112. More specifically, if the density sensed by mass meter 30 approaches the density of water, an alarm will be indicated on the operator interface 68 and, further, the CPU will automatically actuate valve 36 to its second position such that no more oil is flowing into vessel 14, but the oil is instead circulating through conduit 50. Again, at this point, an operator must make the determination whether or not to continue loading oil from this particular lease tank. If alarms are present, the CPU will return to its main program as indicated at 113 until instructed otherwise. During loading, the CPU will also check to make sure the driver has not manually stopped the loading process as indicated at 114.

In addition to temperature, density and flow rate values being collected by the mass meter during transfer, sampling device 38 is also actuated by the CPU 62 at the start of transfer. More specifically, solenoid 44 is actuated in pulses such that it will meter off approximately two cubic centimeters of crude oil for every barrel of oil passing through line section 20. Therefore, for every barrel of oil passing through line section 20, a two cubic centimeter sample is taken. Container 46 is preferably of a size that can approximately take samples from 180 barrels of oil, which is the typical size of a transport vessel 14.

The transfer of oil from storage tank 16 to vessel 14 will continue to take place until such time as the CPU determines from readings of mass meter 30 that the maximum number of barrels has been transferred to transport vessel 14. At this time, the CPU will automatically switch valve 36 to its second position such that oil is circulating through conduit 50. The CPU will also indicate to the operator through interface 68 that transfer has been completed. In addition to switching the CPU actuating valve 36 to its second position, the CPU can also send a signal to sampling device 38 telling it to stop taking samples. After the driver receives the indication that loading is complete, the operator can push a stop button on interface 68 which basically turns off pump 27. It is also possible to have a separate level detection system in vessel 14, which when the oil therein reaches a particular level sounds a horn which indicates that the operator should return to cab 64 of vehicle 12 to monitor the transfer process.

Therefore, throughout the transfer of oil from tank 16 to vessel 14, a gross volume of oil has been computed by CPU 62 from readings taken by mass meter 30. Because the temperature and density readings are taken continuously by the mass meter (as opposed to being taken at only one particular level in a storage tank as was done in the past) the gross volume reading represents a very accurate assessment of the total volume.

With reference to FIG. 3, after the gross volume has been calculated, as indicated at 116, and after the driver has indicated that loading should be stopped as shown at 118, it is now time to determine the basic sediment and water values of the load. More specifically, an operator will now go to sample device 38 and remove container 46. Container 46 houses an oil sample that is representative of all the barrels of oil transferred from tank 16 to vessel 14. The operator then centrifuges the oil therein and takes the appropriate sediment and water sample in a manner that is known in the art. Thereafter, the operator is prompted to enter the sediment and water values manually taken from the oil in container 46 into the CPU as generally indicated at 120. The CPU then utilizes the sediment and water values to calculate a net volume of the oil based on these values. This net volume, along with lease information, destination information, time information, temperature and density information, and driver information can be printed on a ticket which can be left at the leasehold or sent to the oil producer or landowner. The step of calculating the net volume and printing the ticket is generally represented at 122. After the ticket is printed, the CPU returns to its main program, as shown at 124, and is thereafter ready to collect more oil from other leaseholds.

As is apparent, the measurement system 10 has numerous advantages over the prior loading systems in use. More specifically, the sample taken by sampling device 38 gives an incredibly more accurate reading of the basic sediment and water values than the prior system for taking a sample. More specifically, the sample collected in container 46 represents an incremental sample of each and every barrel that has been loaded onto transport vehicle 12. Additionally, rather than take temperature and density readings for the oil in tank 16 at one level only, mass meter 30 takes continuous temperature and density readings, thus providing a much more accurate representation of the volume being transferred from tank 16 to vessel 14. Additionally, because measurements are not based on the oil initially present in tank 16 and the oil present in tank 16 after transfer, adhesion of oil to the side walls of the tank is not a factor. Still further, again because the oil is measured during transfer, interpolation due to encrustation of the tank and the inherent inaccuracies thereof are not present. More specifically, it becomes unnecessary to gauge the amount of encrustation on a tank based upon the amount of encrustation on the vent lid, because the volume measurement is not based on the tank itself. Still further, the recirculation circuit of the present invention and the air eliminator structure 22 increase the accuracy of measurement system 10 in a unique and nonobvious way. Lastly, because system 10 is a completely enclosed system that does not require an operator to ever climb up onto the tanks and have access to the interior of the tanks, there is no possible way for the driver to be exposed to $H_2S$. Such a system could obviate the need to don safety equipment at all, and, further, could obviate the need to have two operators in order to collect crude oil from a leasehold, due to high sulfur oil.

From the foregoing, it will be seen that this invention is one well adapted to attain all the ends and objects hereinabove set forth together with other advantages which are obvious and which are inherent to the structure. It will be understood that certain features and subcombinations are of utility and may be employed without reference to other features and subcombinations. This is contemplated by and is within the scope of the claims. Since many possible embodiments may be made of the invention without departing from the scope thereof, it is to be understood that all matter herein set forth or shown in the accompanying drawings is to be interpreted as illustrative and not in a limiting sense.

We claim:

1. A system for measuring crude oil as it is transported from a storage tank to a transport vessel of a transport vehicle, the system comprising:

an oil conveying line adapted to convey oil from the storage tank to the transport vessel;

a pump associated with said line to convey oil from the tank to the transport vehicle;

a mass meter associated with said line, said mass meter capable of sensing characteristics of the conveyed oil;

a microprocessor controlling said mass meter and utilizing said sensed characteristics so as to calculate the volume of oil transferred from the storage tank to the transport vessel;

a recirculation conduit having a first end in fluid communication with said line on an input side of said mass meter and a second end in fluid communication with said line on an output side of said mass meter; and a diverting valve controlled by said microprocessor and coupling said conduit second end to said line, said diverting valve having a first position allowing flow into the transport vessel and blocking flow into said conduit and a second position blocking flow to the transport vessel and allowing flow into said conduit.

2. The system of claim 1 further including a check valve disposed in said conduit, said check valve only allowing flow in a direction from said second end to said first end of said conduit.

3. The system of claim 1 wherein said conduit first end is attached to said line at a location on the suction side of said pump.

4. The system of claim 1 further comprising an air elimination means disposed in said line between said conduit first and second ends.

5. The system of claim 4 wherein said air elimination means is an air elimination tank disposed in said line, said tank having an input port and an output port, said inlet port being vertically above said output port.

6. The system of claim 1 wherein said microprocessor determines whether water is flowing in the line from the characteristics sensed by said mass meter, said microprocessor having a display means for indicating to an operator that water is flowing in the line.

7. The system of claim 1 wherein said microprocessor determines whether water is flowing in said line from the characteristics sensed by said mass meter, said microprocessor controlling said diverting valve in response to the sensing of water in said line so that said diverting valve switches from its first position to its second position to prevent water from entering the transport vessel.

8. A method for measuring crude oil as it is transported from a storage tank to a transport vessel of a transport vehicle, the method comprising:

directing the oil through a mass meter as it is transferred from the storage tank to the transport vessel, said mass meter sensing predetermined parameters of the oil;

conveying said sensed parameters to a microprocessor where a volume value is computed;

determining based upon the sensed parameters whether water is present in the oil being conveyed to the transport vessel; and diverting the oil being conveyed through a recirculation conduit if water is present.

9. A method for measuring crude oil as it is transported from a storage tank to a transport vessel of a transport vehicle, the method comprising:

directing the oil through a mass meter as it is transferred from the storage tank to the transport vessel, said mass meter sensing predetermined parameters of the oil;

conveying said sensed parameters to a microprocessor where a volume value is computed; and recirculating the oil through a recirculation conduit and an air eliminator structure prior to loading of the oil into the transport vessel.

10. The system of claim 1 wherein said recirculation conduit and said diverting valve are located on the transport vehicle.

* * * * *